US011299516B2

(12) United States Patent
Cohen

(10) Patent No.: US 11,299,516 B2
(45) Date of Patent: Apr. 12, 2022

(54) DAGRS: DIRECTED ANTIGONISTS TO CANCER CELL GROWTH SIGNALS

(71) Applicant: David I. Cohen, Pelham, NY (US)

(72) Inventor: David I. Cohen, Pelham, NY (US)

(73) Assignee: David I. Cohen, Mansfield, MA (US)

( * ) Notice: Subject to any disclaimer, the term of this patent is extended or adjusted under 35 U.S.C. 154(b) by 4 days.

(21) Appl. No.: 15/649,515

(22) Filed: Jul. 13, 2017

(65) Prior Publication Data

US 2018/0016305 A1 Jan. 18, 2018

Related U.S. Application Data

(60) Provisional application No. 62/362,254, filed on Jul. 14, 2016.

(51) Int. Cl.

| | |
|---|---|
| ***C07K 14/005*** | (2006.01) |
| ***A61K 38/00*** | (2006.01) |
| ***C12N 9/12*** | (2006.01) |
| ***G16B 30/00*** | (2019.01) |
| ***G16B 20/30*** | (2019.01) |
| ***G16B 30/10*** | (2019.01) |
| *G16B 20/00* | (2019.01) |
| *G16B 40/00* | (2019.01) |

(52) U.S. Cl.

CPC .............. *C07K 14/005* (2013.01); *C12N 9/12* (2013.01); *C12Y 207/11001* (2013.01); *G16B 20/30* (2019.02); *G16B 30/00* (2019.02); *G16B 30/10* (2019.02); *A61K 38/00* (2013.01); *C07K 2319/09* (2013.01); *C12N 2740/15022* (2013.01); *C12N 2740/15033* (2013.01); *C12N 2740/15051* (2013.01); *C12N 2740/16022* (2013.01); *C12N 2740/16033* (2013.01); *C12N 2740/16051* (2013.01); *G16B 20/00* (2019.02); *G16B 40/00* (2019.02)

(58) Field of Classification Search

None

See application file for complete search history.

(56) References Cited

FOREIGN PATENT DOCUMENTS

WO WO-2009148896 A2 * 12/2009 ............. A61K 45/06

OTHER PUBLICATIONS

Testa et al. ("AKT signaling in normal and malignant cells," Oncogene vol. 24, pp. 7391-7393(2005)) (Year: 2005).*

Johnson et al. ("Targeting the RB-E2F pathway in breast cancer," Oncogene vol. 35, pp. 4829-4835(2016)) (Year: 2016).*

Simon et al. ("Targeting AKT with the Pro-apoptotic Peptide, TAT-CTMP: a Novel Strategy for the Treatment of Human Pancreatic Adenocarcinoma," Int J Cancer. Aug. 15, 2009; 125(4): 942-951; NIH Public Access Manuscript pp. 1-25) (Year: 2009).*

* cited by examiner

*Primary Examiner* — Christina Bradley

(74) *Attorney, Agent, or Firm* — Joseph F. Aceto, Esq.

(57) ABSTRACT

The present invention describes a unique method of treating cancer with the administration of an improved DAGRS™ construct which functions as a humanized agent specifically targeting cancer cells in vivo. A specific DAGRS™ is described constructed of a humanized drug delivery biologic, carboxyl to an Apoptin fragment consisting of Apoptin's proline-rich SH3-binding fragment, a spacer, and a MAP kinase (MAPK) phosphorylation site, in replacement of the SH3-binding domain at HIV-1 TAT's amino terminus. Apoptin is a viral protein with incumbent immunogenicity and toxicity in humans. Improved DAGRS™ constructs are described that replace the viral VP3 peptide with human AKT peptide or derivative, all equivalently spaced 11 amino acids from the initial proline to the beginning of the MAPK phosphorylation site, through which technology the DAGRS™ is fully humanized. DAGRS™ provide for improved bioavailability, enhanced specific activity, and low toxicity for in vivo treatment of cancer. DAGRS™ are a superior method for targeting any oncogene with an inhibitory peptide.

An algorithm for "humanization" is described through which human functional equivalent(s) to viral product(s) are identified by alignment of peptides anchored at each end by matching functional motifs that are spaced equivalently distant in the two aligned peptides. The algorithm totally disregards the primary amino acid composition of the spacer, and as such separates from current computer algorithms that prioritize primary amino acid alignments. Accounting for spacing dictates that functional domains be oriented correctly in three dimensions. The invention taught here can be developed into computer algorithms for rapidly identifying these anchored alignments, and thereafter developing safe humanized drugs from disruptive viral activities. Computers once taught the basic rules for anchoring equivalents, can improve on the basic algorithm through artificial intelligence to expand drug development.

10 Claims, 6 Drawing Sheets

Specification includes a Sequence Listing.

Humanized Tat derivatized/deleted for toxic sequences

SEQ ID 1 FTR KGLGISYGRK KRRQRRR (aa38-57) from HIV1 Tat SF2
SEQ ID 2 RK KRRQRRR
SEQ ID 3 TSEELRKRREAYFEK (aa 277–291) from human Atx-3

SEQ ID 4 CLTKGGVCWG PCTGGFRQIG TCGLPRVRCC
C rich domain (aa41-60) from human βdefensin 4
SEQ ID 5 CRCVFHWCCYVSCQEC
C rich domain from human wnt3

Figure 2

Conservative colour-coded amino acid conservation scoring performed by PRALINE based alignment from 0.1 most conserved alignment position to unconserved for Sooty Mangabey, AGM and Wild Born Mandr.

$NH_2$ Terminus of SIV encode a variety of Transcription Factor Peptide (TFP) Domains expressed in monocyte-macrophage lineage

Figure 3

Conservative colour-coded amino acid conservation scoring performed by PRALINE based alignment from 0.1 most conserved alignment position to unconserved for HIV1 Savanna Chimp and HIV2.

Signal Transducing Canonical SH3 Binding Domain @ $NH_2$ Terminus of HIV-1 Tat

Cells incubated in 10 μM GFP-Tat Monomer

Figure 6

A. <u>16 mers</u>

SEQ ID 6 PKPPSKKRSCDPSEYR

DAGRS™ peptide derived from chicken anemia virus VP3

SEQ ID 7 PPFKPQVTSETDTRYF

DAGRS™ peptide derived from the SH3 binding region of human AKT

SEQ ID 8 PPKPPQVTSETDTRYF (src)

DAGRS™ peptide derived from AKT modifed to be "right-handed" as VP3 and to contain a canonical PPxPP Src SH3-binding site.(Kay, Williamson, and Sudol, FASEB J 14, 231,2000.

B. <u>Original sequence of Bertino et al.</u>

SEQ ID 9 HHHRLSH

DAGRS™ encoding the E2F promoter binding peptide as described by Bertino et al.

Figure 7

AKT functional alignment with VP3

-PKPPSKKRSCDPSEYR from CAV VP3(SEQ ID NO.6)
-PPFKPQVTSETDTRYF from AKT (SEQ ID NO. 7)

SEQUENCE LISTING

<160> NUMBER OF SEQ ID NOS: 9

<210> SEQ ID NO 1
<211> LENGTH: 20
<212> TYPE: PRT
<213> ORGANISM: Human immunodeficiency virus

<400> SEQUENCE: 1

Phe Thr Arg Lys Gly Leu Gly Ile Ser Tyr Gly Arg Lys Lys Arg Arg
1               5                   10                  15

Gln Arg Arg Arg
            20

<210> SEQ ID NO 2
<211> LENGTH: 9

-continued

```
<212> TYPE: PRT
<213> ORGANISM: Homo sapiens

<400> SEQUENCE: 2

Arg Lys Lys Arg Arg Gln Arg Arg Arg
1               5


<210> SEQ ID NO 3
<211> LENGTH: 15
<212> TYPE: PRT
<213> ORGANISM: Homo sapiens

<400> SEQUENCE: 3

Thr Ser Glu Glu Leu Arg Lys Arg Arg Glu Ala Tyr Phe Glu Lys
1               5                   10                  15


<210> SEQ ID NO 4
<211> LENGTH: 30
<212> TYPE: PRT
<213> ORGANISM: Homo sapiens

<400> SEQUENCE: 4

Cys Leu Thr Lys Gly Gly Val Cys Trp Gly Pro Cys Thr Gly Gly Phe
1               5                   10                  15

Arg Gln Ile Gly Thr Cys Gly Leu Pro Arg Val Arg Cys Cys
            20                  25                  30


<210> SEQ ID NO 5
<211> LENGTH: 16
<212> TYPE: PRT
<213> ORGANISM: Homo sapiens

<400> SEQUENCE: 5

Cys Arg Cys Val Phe His Trp Cys Cys Tyr Val Ser Cys Gln Glu Cys
1               5                   10                  15


<210> SEQ ID NO 6
<211> LENGTH: 16
<212> TYPE: PRT
<213> ORGANISM: Chicken anemia virus

<400> SEQUENCE: 6

Pro Lys Pro Pro Ser Lys Lys Arg Ser Cys Asp Pro Ser Glu Tyr Arg
1               5                   10                  15


<210> SEQ ID NO 7
<211> LENGTH: 16
<212> TYPE: PRT
<213> ORGANISM: Homo sapiens

<400> SEQUENCE: 7

Pro Pro Phe Lys Pro Gln Val Thr Ser Glu Thr Asp Thr Arg Tyr Phe
1               5                   10                  15


<210> SEQ ID NO 8
<211> LENGTH: 16
<212> TYPE: PRT
<213> ORGANISM: Homo sapiens

<400> SEQUENCE: 8

Pro Pro Lys Pro Pro Gln Val Thr Ser Glu Thr Asp Thr Arg Tyr Phe
1               5                   10                  15


<210> SEQ ID NO 9
```

-continued

```
<211> LENGTH: 7
<212> TYPE: PRT
<213> ORGANISM: Homo sapiens

<400> SEQUENCE: 9

His His His Arg Leu Ser His
1               5
```

DAGRS: DIRECTED ANTIGONISTS TO CANCER CELL GROWTH SIGNALS

CROSS-REFERENCE TO RELATED APPLICATIONS

This application claims the benefit of U.S. Provisional Application No. 62/362,254, filed Jul. 14, 2016 and incorporated by reference in its entirety.

FIELD OF THE INVENTION

The present invention relates to the field of oncogene-targeted therapeutics in the treatment of cancer.

BACKGROUND

Cancer is among the leading causes of morbidity and mortality worldwide with approximately 14 million new cases and 8.2 million cancer-related deaths in 2012 (WHO, World Cancer Report. Bernard W. Stewart and Christopher P. Wild, eds. 2014). The number of new cases is expected to rise by about 75% over the next 2 decades coincident with an aging population. One defining feature of cancer is the rapid creation of abnormal cells that grow beyond their usual boundaries, and which can then invade adjoining parts of the body and spread to other organs. Oncogenesis is the result of the interaction between genetic factors and external agents such as, but not limited to, ultraviolet radiation, asbestos tobacco smoke, or viral infection. Cancer-causing viral infections such as HBV/HCV and HPV are responsible for up to 20% of cancer deaths in low- and middle-income countries The transformation from normal cells into tumor cells is a multistage process, typically a progression from a pre-cancerous lesion seeded by cancer stem cells, to malignant tumors that metastasize to distant sites. Metastasis is the primary cause of death for human cancers, while certain cancers that rarely metastasize (basal cell carcinoma) are almost never fatal.

Current cancer treatments are dominated by invasive surgery, radiation therapy and chemotherapy protocols, which are frequently ineffective and can have potentially severe side-effects, non-specific toxicity and/or cause traumatizing changes to an individual's body image and/or quality of life. One of the causes for the inadequacy of current cancer treatments is their lack of selectivity for affected tissues and cells. More selective cancer treatments would leave normal cells unharmed thus improving outcome, side-effect profile and quality of life.

While significant advancements have been made, treatment of cancers by chemotherapy frequently results in severe side effects because the therapy used is not specific to the cancer, killing non-cancerous cells including hematopoietic cells critical to immune surveillance. In addition to standard chemotherapy and hormone replacement therapy, new classes of therapies have emerged with directed oncolytic mechanisms. One approach targets either toxins or radioactive isotopes directly into the cancers by coupling the oncolytic agent to monoclonal antibodies (MAb) directed against cancer antigen. Genentech's Kadcyla® is an example of this kind of "smart-bomb" approved for the treatment of breast cancer. Another class are drugs like Gleevec® (Novartis) that antagonize growth pathways specific to cancer cells, such as the bcr-abl oncogene of chronic myelogenous leukemia targeted by Gleevec®. This is the class of agent described in this invention, with the difference that this invention describes a biologic that is a drug delivery tool with a programmable cassette such that it can be theoretically targeted against any oncogene. Other approaches are being designed directed against growth pathways specific to cancer stem cells, which are the seeds for cancer metastasis to distant sites. This stem cell strategy is a preferred realization of this invention because it has been theorized that mutational escape of cancer stem cells is rare compared to cancer tumor cells.

Other realizations of targeted cancer therapies are oncolytic viruses, a technology based on the observation by Coley of spontaneous remissions in certain blood cancers during severe systemic viral infections. Oncolytic viruses are currently approved for the treatment of certain blood dyscrasias and recurrent melanoma Kyprolis® (Amgen, Inc.) or carfilzomib for injection for multiple myeloma, see U.S. Pat. Nos. 9,315,542 and 9,309,283. Most recently an oncolytic poliovirus developed at Duke Medical Center gained fast track approval for the treatment of recurrent glioblastoma. The Chicken Anemia Virus (CAV) has been noted to mediate oncolysis through its VP3 ("Apoptin") protein, an observation that has remained in pre-clinical development owing to bioavailability and delivery issues.

At the present time, patients with recurrent cancer have few options of treatment that offer extended quality of life. The regimented approach to cancer therapy has produced overall improvements in global survival and morbidity rates. However, to the particular individual, these improved statistics do not necessarily correlate with an improvement in their personal situation, or even to prolonged survival. When cancer recurs after these consolidation therapies, it is almost always rapidly fatal even when treated by any of the newer targeted agents.

An improved approach to treatment would be to design agents targeted to inhibiting oncogenes using Directed Antagonists to cancer Growth Signals or DAGRS, with low toxicity and good bioavailability. This invention captures the cancer-killing activity of certain oncolytic viruses in a simple peptide, sparing the toxicities associated with a multitude of other viral proteins that are superfluous to oncolysis but a source of toxicity. In the example of oncolyitc poliovirus for glioblastoma, the investigators had the profound head start to safety of an attenuated poliovirus that has been used safely for 60 years as a vaccine. While its approval for use in adult glioblastoma is a major advance, glioblastoma is also a disease of children. The coupling of the historically higher incidence of paralytic polio in children with the global immune suppression associated with cancers raises the concern that the safety profile of the oncolytic poliovirus may not be nearly as good in children as it is in adults.

The treatment of diverse cancers with the power and adaptability of DAGRS is a major beneficial outcome that can derive from this invention. As one example, individual profiling of cancers is becoming commonplace as a strategy to better tailor therapeutics to the unique genetics of the patient. Because in principle DAGRS can be targeted against any oncogene, a pair or even a trio of synergistic DAGRS could be administered to the cancer patient that precisely antagonize that individual's oncogene profile. As a second example, mutations have been discovered that render some fraction of cancers particularly susceptible to specific directed oncolytics. Invariably the cancers under treatment undergo mutational escape so that, while there is a short term benefit in tumor regression, the long term benefit in survival is most frequently marginal. Because the downstream escape pathways are limited and reproducible, a DAGRS that targets and blocks the most common downstream escape mechanism(s) could be administered along with another directed oncolytic, thereby potentiating the efficacy of both.

SUMMARY

The present invention describes an improved composition and methods for the treatment of cancer that incorporate the administration of a synthetic, genetically engineered Directed Antagonists to cancer Growth Signals or DAGRS targeted at inhibiting an oncogene. Because DAGRS are constructed from diverse small stretches of genetic material that are tiled together in a unique arrangement, DAGRS compositions of matter have less than 50% homology to any naturally occurring biologic. DAGRs have the ability to deliver a biologic from outside the cell through the cytoplasm to the nucleus, and are engineered to bind to specific targets through introduction of specific peptide fragments into a cassette that locks the peptide into a high affinity configuration. DAGRS can in principle be targeted against any oncogene. Preferred oncogene targets illustrated in this invention are E2F and AKT, which are effective against many cancers in vitro. AKT is a particularly attractive target because it is found to be mutated in approximately 80% of human cancers, its inhibition mediates a p53 independent apoptosis, and its specific activity in G2 phase dividing (cancer) cells supports a good safety profile for normal cells. The CAV VP3 protein ("Apoptin") mediates oncolysis at least in part through AKT, and Apoptin has been shown to kill a wide variety of cancer cells but not normal cells in vitro. Apoptin has been coupled to Tat monomer as an in vitro delivery tool with positive results. However, the toxicities inherent in native HIV Tat monomer, as well as the general instability of peptides linked together side by side as investigated, render this design unsuitable for in vivo use and clinical application owing to safety problems. DAGRS use two inherent properties of Tat, one that locks a signal-transducing peptide into an active conformation within the first 20 amino acids of the protein, making for the cloning cassette, and the well-described TAR and RK-rich membrane translocation sequence (aa 38-60 of SF2 Tat). An SH3 binding domain described here naturally encoded at the amino terminus of HIV-1 Tat is removed from the cassette, and inhibitory peptides for eg AKT or E2F are swapped into the cassette. As we have discovered that this SH3-binding domain is a major source of toxicity, in this process DAGRS are rendered much safer than Tat. A CRD that sits just carboxyl to the cassette, and is a major source of Tat reactivity, is "humanized" to remove toxicity by replacement alternatively with a human C-rich spacer, or the CRD from non-pathogenic SIV Tat. Because the present invention appreciates that DAGRS affinity for signal-transducing target is a property of its conformation, and that DAGRS bioavailability depends upon membrane translocation, the DAGRS described in the present invention preserves both of these functionalities. These DAGRS constructs provide improved safety and better bioavailability for therapeutics in the treatment of cancer and other in vivo applications.

DESCRIPTION OF THE FIGURES

FIG. 2: An amino acid conservative alignment in Sooty Mangabey, AGN and Wild born Manfdr of $NH_2$ terminal sequences of SIV Tats with homology to transcription factors. PRALINE program was used to generate the alignments.

FIG. 3: An amino acid conservative alignment of $NH_2$ terminal sequences of HIV and CPZ Tat containing a P-rich string with homology to SH3-binding domains.

FIG. 6: Compositions of Matter encoding oncogene-antagonizing peptides.

```
SEQ ID NO: 6
PKPPSKKRSCDPSEYR
```

DAGRS peptide derived from chicken anemia virus VP3

```
SEQ ID NO: 7
PPFKPQVTSETRYF
```

DAGRS peptide derived from the SH3-binding region of human AKT

```
SEQ ID NO: 8
PPKPPQVTSETDTRYF
```

DAGRS peptide derived from AKT modified to be "right-handed" as VP3 and to contain a canonical PPxPP Src SH3-binding site. (Kay, Williamson, and Sudol, FASEB J 14, 231, 2000).

```
SEQ ID NO: 9
HHHRLSH
```

DAGRS encoding the E2F promoter binding peptide as described by Bertino.

FIG. 7: Algorithm for Humanizing a viral peptide. in silico identification of the apoptotic determinant in CAV VP3 as a peptide homologous to the SH3-binding domain of AKT. The alignment is anchored by a P-rich SH3-binding region (Orange box) at its amino end, and anchored at its carboxyl end by an S/TxY (blue and green boxes) MAP kinase phosphorylation motif.

DETAILED DESCRIPTION OF THE INVENTION

DAGRS are targeted drugs aimed to control tumor growth, and prevent or resolve metastases, while avoiding many of the side effects associated with standard chemotherapy.

Figure 1:
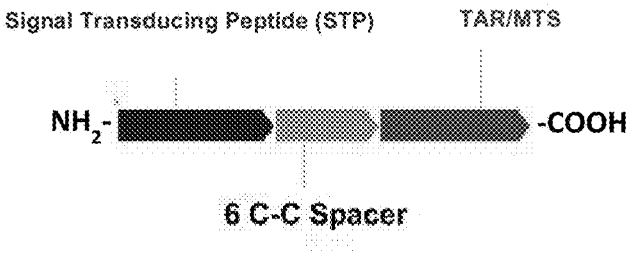
FIG. 1: Schematic of DAGRS constructs. Illustrated are the 3 genetic components ("tiles") of a DAGRS construct: 1) an $NH_2$ terminal cassette encoding a signal transducing peptide (STP) designed to competitively inhibit an oncogene, a C-Rich spacer preferentially encoding 6 cysteine residues, that facilitates proper folding of the DAGRS, and a RK-rich membrane translocation sequence (MTS), SEQ ID NO:2) at the COOH terminus that is preceded by sequences interacting with cyclin (TAR, SEQ ID NO:1, underlined) or other proteins that translocate from the cytoplasm to the nucleus. The entire third cassette could also be replaced by fully human sequences, such as amino acids 277 to 291 from Atx-3 that mediates interaction with human VCP with nuclear translocation of the complex. (Boeddrich et al. EMBO J 25, 1547, 2006.) Although modelled after the molecular design of Tat, either 0 or 1 of three DAGRS domains contain Tat sequences, permitting the approximation that DAGRS hold an overall homology to HIV Tat between 0-33%.

The present invention provides for improved oncogene-directed biologics which in its simplest realization locks a signal transducing peptide into an $NH_2$ terminal cassette in a biologically active configuration protected from degradation, and links this sequence to a carboxyl KR-rich membrane translocation sequence (MTS, SEQ ID NO:2). The construct is designed to facilitate bioavailability and stability of the oncogene-inhibitory peptide. The Tat-encoded membrane translocation sequence (SEQ ID NO:2, "penetrin") has been screened for safety in clinical trial (Voskens et al. Head Neck 34, 1734, 2012). Additionally, Tat contains sequences critical for its entering the nuclear transcriptome (TAR) and to its binding cyclin (SEQ ID NO:1, underlined) that are a preferred realization of this invention (SEQ ID NO:1), because they are proposed to maintain all functionalities while conserving correct domain spacing within Tat. It is not known whether TAR (aa 38-47 within Tat) contributes to Tat toxicity, so another realization of this invention preferred for safety replaces Tat TAR/MTS with a fully human sequence studied to have similar functionalities as Tat. As an example, human Atx-3 mediates the translocation of human VCP to the nucleus: the peptide sequence responsible for these functionalities is illustrated (Atx-3 amino acids 277-291, SEQ ID NO:3). Noteworthy that like Tat SEQ ID NO:3 encodes a short stretch of amino acids preceding its KR-rich MTS. A schematic of the DAGRS construct is illustrated in FIG. 1.

DAGRS use a molecular design evolved by the SIV/HIV Tat protein, but are humanized for safety. Overall, DAGRS composition of matter range between 0-33% identity to Tat. This is critical because HIV Tat is a toxic substance which precludes its use in clinical applications. Following the molecular design of SIV Tat (FIG. 2) and HIV/CPZ Tat (FIG. 3), DAGRS contain a signal transducing peptide (STP) at their $NH_2$ terminus. The natural STP of the Tat design is removed, leaving behind a cassette for inserting a peptide theoretically capable of inhibiting any oncogene dependent on the sequence of the STP. An important embodiment of the present invention contemplates replacement of the Tat CRD ligand combining site with a neutral human genetic spacer of relatively similar composition, and in particular containing 6 C residues to facilitate proper folding of the biologic. Two examples illustrating this invention are the CRD (amino acids 41-60) from human β-defensin 4 (SEQ ID NO:4) or the CRD from human wnt3 (SEQ ID NO:5), although any human CRD pairing 6 C is a preferred realization of this invention. Without modification, the CRD region, which is very autoreactive, could cause major toxicity. Therefore the present invention has redesigned ("humanized") the region to provide for significantly less toxicity.

FIG. 2 shows an alignment of acidic transcription factor peptides (TFP) encoded at the $NH_2$ terminus of SIV. The sequences are stapled on one side by the M initiator and move directly into a DE-rich (acidic transcription activator) segment. The SIV TFP are locked into configuration by a conserved P at their COOH end just before the start of the CRD, as illustrated in FIG. 2. FIG. 3 demonstrates that HIV-1, HIV-2, and CPZ carry a different class of STP at their $NH_2$ terminus with characteristics of SH3-binding domains. In particular these three Tat STP initiate with a PxxP motif canonical for SH3-binding domains. As for SIV Tat, they are stapled at their COOH end by another P just prior to the C-rich domain (FIG. 3).

Figure 4:
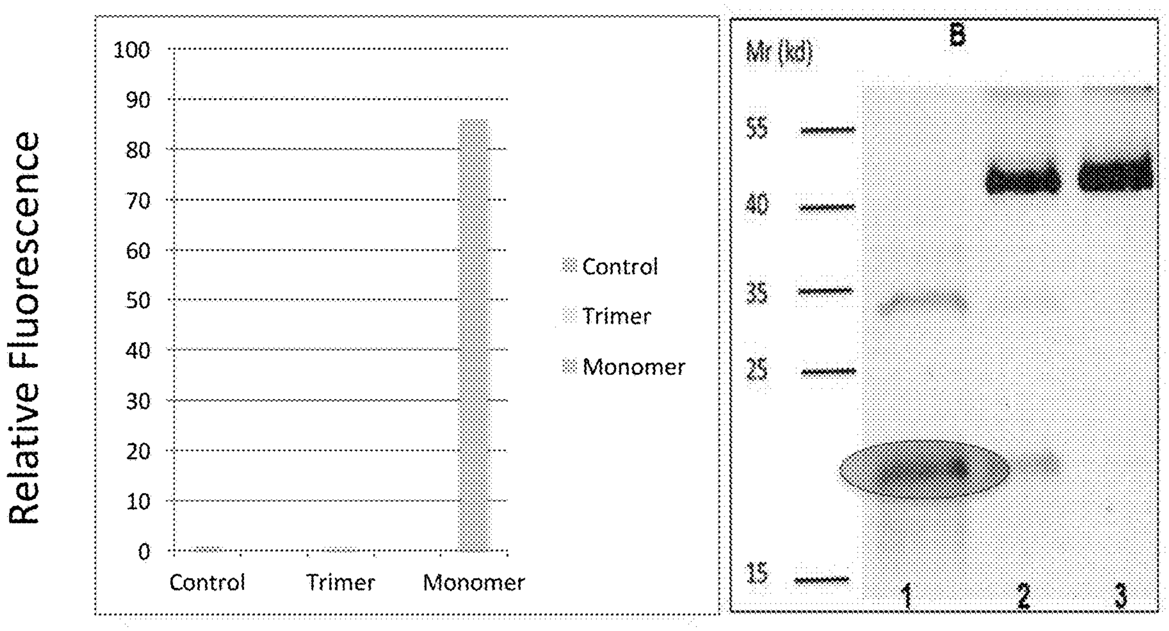
FIG. 4: Monomer Tat transcriptional activation of the HIV lir. A. Graph of induced luciferase activity. HeLa cells were transfected with an HIV LTR luciferase reporter construct. 24 hours after transfection at a time when cells were approximately 75% confluent, cells were scrape-loaded with 2 μg protein in the presence of 100 μM chloroquine as described by Frankel (Frankel AD1, Pabo CO.Cell. 1988 Dec. 23; 55(6):1189-93) After an additional 24 hours luciferase activity was measured and is recorded as relative activity compared to sham-transfected HeLa cells. The average of three independent experiments is shown. B. Western blot of recombinant Tat proteins synthesized in *E. coli* probed with polyclonal antibodies from mice receiving Tat immunotherapy, Monomeric Tat was isolated directly from cracked cells ((Lane 1), or Tat proteins were sequentially re-annealed to trimer (Lanes 2,3) by incubation with polyclonal antibody to aa 57-72 peptide (HIV1 SF2). Molecular weight in kilodaltons (MrKd). Trimeric Tat runs as an apparent 48 kd substrate and monomer as 16 kd; wherever monomer is present at high concentrations, cysteine-linked dimers are also observed (Lane 1).

FIG. 4 shows the well-known property of monomeric Tat to enter into and influence cellular transcription. The TAR region (SEQ ID NO:1, underlined) and the MTS are critical components of this functionality. In particular, HeLa cells loaded with 2 μg monomeric Tat protein transactivated an ltr-luciferase construct 85 fold above sham-loaded HeLa cells, or HeLa loaded with 2 μg trimeric Tat, which is the biologically active form for oncoimmunotherapeutics. Tat provides the means to introduce the oncogene-inhibitory STP fragment at the site of action. FIG. 4 shows the activity of the monomer as a transcriptional regulator.

Figure 5:
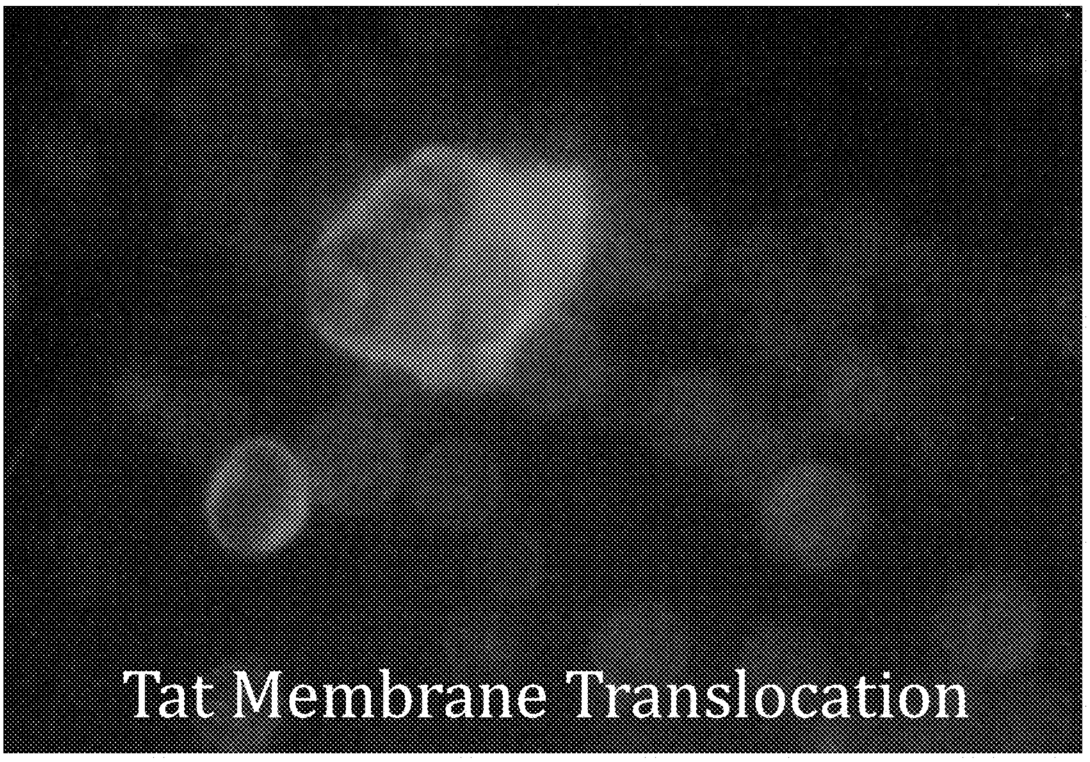
FIG. 5: Bioavailability of Tat after membrane translocation. Peripheral blood mononuclear cells (PBMCs, $10^6$ cells/ml) were activated with phytohemagglutinin (PHA, 10 μg/ml) for 48 hours. PBMCs were washed, re-suspended at $10^7$ cells/ml, and scrape-loaded with Tat genetically linked to Green Fluorescent Protein (Tat-GFP, 10 μM). PBMCs were diluted back to $10^6$ cells/ml and cultured overnight (15 hours) in RPMI-10% FCS at which time they were harvested and assayed for green fluorescence.

The present invention further improves bioavailability by combining the membrane translocation sequences of Tat with the targeted killing effect of Apoptin, or any STP. The invention is not interfered with by patent filings proposing to link Apoptin to Tat for improved bioavailability (US 20020176860, US 2008/0234466) because those inventors on the Tat-Apoptin patents acknowledge that native Tat is too toxic to be administered to humans (see Los et al., Apoptin, a tumor-selective killer, Biochem Biophys Acta. 1793, (2009) 1335-1342), and because the DAGRS sequences bear<33% identity to Tat. Translocation of Tat-GFP-monomer is shown in FIG. 5. Here, cells are incubated in 10 micromolar Tat-GFP monomer and fluorescently imaged.

FIG. 6 details specific DAGRS compositions of matter to be embedded into the STD (SEQ ID NO:6-SEQ ID NO:9). In particular, SEQ ID NO:6 proposes a DAGRS with an unmodified 16mer from the CAV VP3 ("Apoptin") that contains the VP3 SH3-binding site and flanking carboxly amino acids. CAV VP3 ("Apoptin"), has been shown to specifically interact with AKT. Apoptin is known to kill most cancers using an AKT pathway, but Apoptin is not cytotoxic for normal cells. Prior to the present invention, nothing similar has been described that could function as an in vivo oncolytic without associated toxicity. SEQ ID NO:7 identifies a 16mer homologue to the VP3 SH3-binding domain and carboxyl flanking sequences in human AKT, strongly supporting the proposal that VP3 functions as a competitive inhibitor to AKT activation. Further, polio oncolytic virus, now approved for treating recurrent glioblastoma cancers, appears to work, at least in part, through an AKT mechanism. The present invention proposes using the human AKT SH3-binding region (SEQ ID NO:7) as an alternative to SEQ ID NO:6 under the proposition that its fully human sequence will be better tolerated and less immunogenic in the clinical setting. A third DAGRS derivative (SEQ ID NO:8) aligns the paired prolines at the carboxyl terminus, as in VP3, but also retains the paired amino prolines, and in so doing creates a DAGRS with a canonical SH3-binding site for the src oncogene. Interaction between Src and the SH3-binding region of AKT is requisite for AKT activation (Jiang and Qiu, Journal of Biological Chemistry 278, 15789, 2003). SEQ ID NO:8 describes a derivatization of AKT peptide that could give it higher affinity for Src than native human AKT. A further realization of the composition is extending 16mer SEQ ID NO:6-SEQ ID NO:8 with 4 or 5 COOH amino acids from their respective proteins (ie RVSEL for VP3), thereby engineering 20mers with proposed carboxyl phosphorylation site anchors more distant from their P staples (FIG. 7), since the P staples are not present in either VP3 or AKT whole protein, and could be a source of steric hindrance.

Another embodiment of the present invention is a DAGRS with a transcription factor/protein activator region such as a peptide capable of binding to E2F promoter ((SEQ ID NO:9). This design bears analogy to SIV Tat in encoding an acidic region, while the AKT design bears analogy to HIV Tat in encoding an SH3-binding domain As for SEQ ID NO:6-SEQ ID NO:8, it could be beneficial to distance E2F peptide (SEQ ID NO:9) by 4 or 5 amino acids from the COOH P staple.

FIG. 7 demonstrates the functional alignment between the viral VP3 SH3-binding domain, and human AKT SH3-binding domain, and establishes an algorithm generally useful for the alignment of viral tiles with human tiles (a "humanization" algorithm). In particular other than the alignment of the proline-rich SH3-binding domains (boxed orange) there is little or no homology (and none recognized by current standard protein alignment programs) until the sequences reach a tightly evolutionarily conserved S/TxY Mitogen Activated Protein kinase phosphorylation site (Mohanta et al Biological Procedures Online 17, 13, 2015) at their COOH end, with an identical spacing of 9 amino acids between P and S/T (boxed blue). Particularly insofar as AKT is known to require Y phosphorylation (by Src) for activation, a reasonable model is that in resting cells S/T is phosphorylated and sterically inhibiting Y (boxed green) phosphorylation carboxyl by 2 amino acids. Upon oncogenic transformation, which is known to induce phosphatases, S/T would become dephosphorylated and Y susceptible to AKT oncogenic phosphorylation. In either case, the VP3 cassette (SEQ ID NO:6) could function as a competitive inhibitor to AKT activation, as would be also expected for the Y phosphorylation sites of SEQ ID NO:7 and SEQ ID NO:8.

This is the first time that a functional viral domain has been matched up ("humanized") to a human protein fragment, and in so doing describes a key humanization invention. The example of FIG. 7 can be generalized to an algorithm that identifies conserved functionalities among proteins (AKT and VP3 both influence G2 phase cell cycle transition and interact with identical proteins), aligns peptides from the two proteins through amino and carboxyl anchors with matched functional domains, eg an SH3-binding domain and a MAP kinase phosphorylation domain, and prioritizes equivalent spacing between the two functional domains, while at the same time totally ignoring the primary amino acid sequence of the spacer. The rationale supporting the algorithm is that correct amino acid spacing conserves functional interactions in three dimensions. The algorithm totally ignores the composition of amino acids intervening between the anchors, because the evolutionary distance between the species originally hosting the virus and humans is proposed to be too distant to conserve primary amino acid sequence of these non-essential residues. This is consistent with the vectors that transmit Zika virus and Ebola virus to humans, being respectively mosquitoes and bats. Many viral activities could be rendered safe and therapeutic via this algorithm converting viral components to human protein components.

Although the present invention has been described with reference to specific embodiments, workers skilled in the art will recognize that many variations may be made therefrom and it is to be understood and appreciated that the disclosures in accordance with the invention show only some preferred embodiments and advantages of the invention without departing from the broader scope and spirit of the invention. It is to be understood and appreciated that these discoveries in accordance with this invention are only those which are illustrated of the many additional potential applications that may be envisioned by one of ordinary skill in the art, and thus are not in any way intended to be limiting of the invention. Accordingly, other objects and advantages of the invention will be apparent to those skilled in the art from the detailed description together with the claims.

What is claimed is:

1. A Directed Antagonist to Cancer Cell Growth Signal (DAGRS) peptide comprising:

(i) an N-terminal signal transducing peptide (STP) that antagonizes an Akt or E2F oncogenic protein, wherein the STP is selected from the group consisting of an apoptin peptide comprising SEQ ID NO: 6, a SH3-binding region peptide of human Akt comprising SEQ ID NO: 7, a SH3-binding site peptide of Human Akt that has enhanced affinity for Src comprising SEQ ID NO: 8, and a peptide capable of binding to an E2F promoter comprising SEQ ID NO: 9;

(ii) a C-terminal KR-rich membrane translocation sequence (MTS); and (III) a spacer that links the N-Terminal STP to the C-terminal MTS, wherein the spacer is a cysteine rich peptide from human ß-defensin 4 comprising SEQ ID NO: 4 or human wnt3 comprising SEQ ID NO:5.

2. The DAGRS peptide of claim 1, wherein the N-terminal STP comprises SEQ ID NO: 8.

3. The DAGRS peptide of claim 1, consisting of the N-terminal STP, the spacer, and the C-terminal MTS.

4. The DAGRS peptide of claim 1, wherein the spacer is derived from the cysteine-rich domain of human ß-defensin 4 and comprises SEQ ID NO:4.

5. The DAGRS peptide of claim 1, wherein the spacer is derived from the cysteine-rich domain of human wnt3 and comprises SEQ ID NO: 5.

6. The DAGRS peptide of claim 1, wherein the C-terminal MTS is an HIV-1 Tat sequence comprising SEQ ID NO: 1.

7. The DAGRS peptide of claim 1, wherein the C-terminal MTS is an ATx-3 sequence comprising SEQ ID NO:3.

8. The DAGRS peptide of claim 1, wherein the C-terminal MTS is a penetrin sequence comprising SEQ ID NO:2.

9. A peptide comprising the amino acid sequence of SEQ ID NO: 8, wherein the peptide inhibits Akt activation and has enhanced affinity to Src.

10. A directed Antagonist to Cancer Cell Growth Signal (DAGRS) comprising:

(i) an N-terminal signal transducing peptide (STP) that antagonizes an Akt oncogenic protein, wherein the STP is a SH3-binding site peptide of human Akt that has enhanced affinity for Src comprising SEQ ID NO:8; and (ii) a C-terminal KR-rich membrane translocation sequence (MTS).

* * * * *